(12) United States Patent
Farnworth

(10) Patent No.: US 6,350,494 B1
(45) Date of Patent: Feb. 26, 2002

(54) METHOD FOR GENERATING CONTINUOUS STREAM OF LIQUID METAL DROPLETS

(75) Inventor: Warren M. Farnworth, Nampa, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 09/339,015

(22) Filed: Jun. 23, 1999

Related U.S. Application Data

(62) Division of application No. 08/989,578, filed on Dec. 12, 1997, now Pat. No. 5,988,480.

(51) Int. Cl.[7] ............................ B05D 1/04; B05B 17/04
(52) U.S. Cl. ...................... 427/469; 427/422; 427/466; 427/468; 427/472; 427/475; 427/564; 427/565; 239/3; 239/4; 239/11; 239/13
(58) Field of Search ................................ 427/421, 422, 427/427, 458, 466, 468, 469, 472, 475, 562, 564, 565; 239/3, 4, 11, 13; 118/56, 57, 620, 624, 640

(56) References Cited

U.S. PATENT DOCUMENTS

| | | | |
|---|---|---|---|
| 4,817,851 A | 4/1989 | Kolesar et al. | |
| 4,981,249 A | 1/1991 | Kawashima et al. | |
| 5,226,948 A | 7/1993 | Orme et al. | |
| 5,259,593 A | 11/1993 | Orme et al. | |
| 5,266,098 A | 11/1993 | Chun et al. | |
| 5,364,011 A | 11/1994 | Baker et al. | |
| 5,377,961 A | 1/1995 | Smith et al. | |
| 5,379,931 A | 1/1995 | Van Schaik | |
| 5,411,602 A | 5/1995 | Hayes | |
| 5,455,606 A | 10/1995 | Keeling et al. | |
| 5,481,288 A | 1/1996 | Keeling et al. | |
| 5,520,715 A | 5/1996 | Oeftering | |
| 5,545,465 A | 8/1996 | Gaynes et al. | |
| 5,560,543 A | 10/1996 | Smith et al. | |
| 5,597,110 A | 1/1997 | Melton et al. | |
| 5,643,353 A | 7/1997 | Wallace et al. | |
| 5,736,074 A | 4/1998 | Hayes et al. | |
| 5,746,844 A | 5/1998 | Sterett et al. | |
| 5,747,102 A | 5/1998 | Smith et al. | |
| 5,772,106 A | 6/1998 | Ayers et al. | |
| 5,779,971 A | 7/1998 | Tsung Pan et al. | |
| 5,810,988 A | 9/1998 | Smith, Jr. et al. | |
| 5,855,323 A | 1/1999 | Yost et al. | |
| 5,868,305 A | 2/1999 | Watts, Jr. et al. | |
| 5,891,212 A | 4/1999 | Tang et al. | |
| 5,894,980 A | 4/1999 | Orme-Marmarelis et al. | |
| 5,894,985 A | 4/1999 | Orme-Marmarelis et al. | |
| 5,938,102 A | 8/1999 | Muntz et al. | |
| 5,988,480 A | 11/1999 | Farnworth | |
| 6,036,777 A * | 3/2000 | Sachs ........................ | 118/56 |
| 6,082,605 A | 7/2000 | Farnworth | |

FOREIGN PATENT DOCUMENTS

SU      1682039      10/1991

* cited by examiner

Primary Examiner—Shrive P. Beck
Assistant Examiner—Jennifer Calcagni
(74) Attorney, Agent, or Firm—TraskBritt

(57) ABSTRACT

A solder jet apparatus is disclosed The solder jet apparatus is a continuous mode solder jet that includes a blanking system and raster scan system. The use of the raster scan and blanking systems allows for a continuous stream of solder to be placed anywhere on the surface in any desired X-Y plane. This allows for greater accuracy as well as greater product throughput. Additionally, with the raster scan system, repairs to existing soldered surfaces can be quickly and easily performed using a map of the defects for directing the solder to the defects.

11 Claims, 2 Drawing Sheets

METHOD FOR GENERATING CONTINUOUS STREAM OF LIQUID METAL DROPLETS

CROSS REFERENCE TO RELATED APPLICATION

This application is a divisional of application Ser. No. 08/989,578, filed Dec. 12, 1997, U.S. Pat. No. 5,988,480, issued Nov. 23, 1999.

BACKGROUND OF THE INVENTION

The present invention relates generally to applying solder to a substrate and, more particularly, to the selected placement of solder using a solder jet.

Depositing solder selectively on a substrate is well known. Different techniques include stenciling or screening a solder paste onto the substrate, using solder balls selectively placed where metal contact is desired, and chemically vapor depositing the metal onto the surface of the substrate. Each one of these methods has advantages and disadvantages.

The use of a stencil to fabricate a conductive trace pattern on the surface allows for precise alignment and placement of the solder. Unfortunately, the stencils are expensive to design and produce and they wear out after repeated use. When they wear out, solder seeps through the worn stencil areas across those areas where no solder is desired, causing shorts, or no solder is being placed where it is needed, causing a breach or open connection. These areas have to be repaired and if these types of conditions are repeated with any type of frequency, the stencil must be replaced with a new stencil. Additionally, stencils require periodic cleaning, which adds another processing step to clean the stencil as well as lessens the useful life of the stencil.

The use of solder balls has been a tremendous advance in the art of electrically connecting a device to the surface of a printed circuit board. Solder balls, however, have quality control problems as their critical dimensions continue to decrease. The ability to produce balls of the same diameter consistently decreases as the diameter decreases. Thus, for some diameters of solder balls, the range of acceptable product can be solder balls having diameters more than twice the desired diameter. Or, they can have diameters half the size of the desired diameter. This requires that the tolerances at the surface contact level of a substrate, such as a semiconductor device, must allow for a solder ball having a diameter that is from 50% smaller to 100% larger than the specified size. Further, working with solder balls is difficult because of their size and the methods needed to place them accurately. When they fail to be placed accurately, or are missing entirely, problems occur in the resulting assembly of a semiconductor device attached to a substrate that must be corrected. These problems include shorts or opens that must be fixed. No easy solution yet exists for repairing missing or improperly sized solder balls after a semiconductor device has been mechanically attached in place on a substrate.

Chemical vapor deposition (CVD) allows for precise alignment of conductive traces and for batch processing. CVD does have limitations however. These limitations include being unable to place the package directly on the surface of the printed circuit board (PCB) immediately after depositing the metal on the surface since a cooling step is typically needed. Further, clean conditions are always necessary when using CVD, which requires expensive equipment and control. Additionally, when clean conditions do not exist, shorts or opens in assemblies can occur that need to be repaired once they are discovered.

A new approach to deposit solder on a surface, such as a printed circuit board (PCB), is to deposit the solder using a solder jet, similar to the manner in which ink jets deposit ink onto paper for printing. The ink jet technology is well established, but due to different problems associated with solder, ink jet technology is not directly applicable to solder jet technology. For example, solder jets use molten melt as a print agent,whereas ink jets use heated water-based ink. Since the print agent is metal in solder jets, the viscosities and densities are much different as are the operating temperatures. Thus, applying ink jet solutions to solder jet problems is impractical.

One typical solder jet apparatus has recently been developed by MPM Corporation. The solder jet apparatus takes liquid solder and forms it into a stream of droplets that have a uniform size and composition. The formation of the droplets involves generating a consistent pressure coupled with a vibration force sufficient enough to dislodge the drops from the jet nozzle in a steady state with a uniform size and consistency. Once the solder droplets are formed, gravity forces them downward where they impact on the surface of the substrate. The solder droplets pass through a charging electrode to impart a charge on the metal droplets.

The system operates using a binary control that either allows the droplets to impact on the surface or to be removed into a droplet catcher for recycling when no droplets are desired. Since the droplets were charged at one point, an electric field or pulse can be asserted, causing the droplets to either continue to the surface or to fall into the catcher. With this system, the exact position of the droplets is known and never varies. Thus, the substrate must be moved to the desired grid for the droplets to impact the area desired to be soldered. This results in a highly inefficient system since the substrate must be stopped for each application of solder to a new location. This also involves greater mechanical complexity since the table holding the substrate, or the solder jet apparatus itself, must be moved and aligned properly before solder can be deposited.

Accordingly, what is needed is a solder applicator that allows for greater precision in placing the droplets along with increased efficiency in product throughput.

SUMMARY OF THE INVENTION

According to the present invention,a solder jet apparatus is disclosed The solder jet apparatus is a continuous mode solder jet that includes a blanking system and raster scan system. The use of the raster scan and blanking systems allows for a continuous stream of solder to be placed anywhere on the surface in any desired X-Y plane. This allows for greater accuracy as well as greater product throughput. Additionally, with the raster scan system, repairs to existing soldered surfaces can be quickly and easily performed using a map of the defects for directing the solder to the defects.

DETAILED DESCRIPTION OF THE INVENTION

Figure 1:
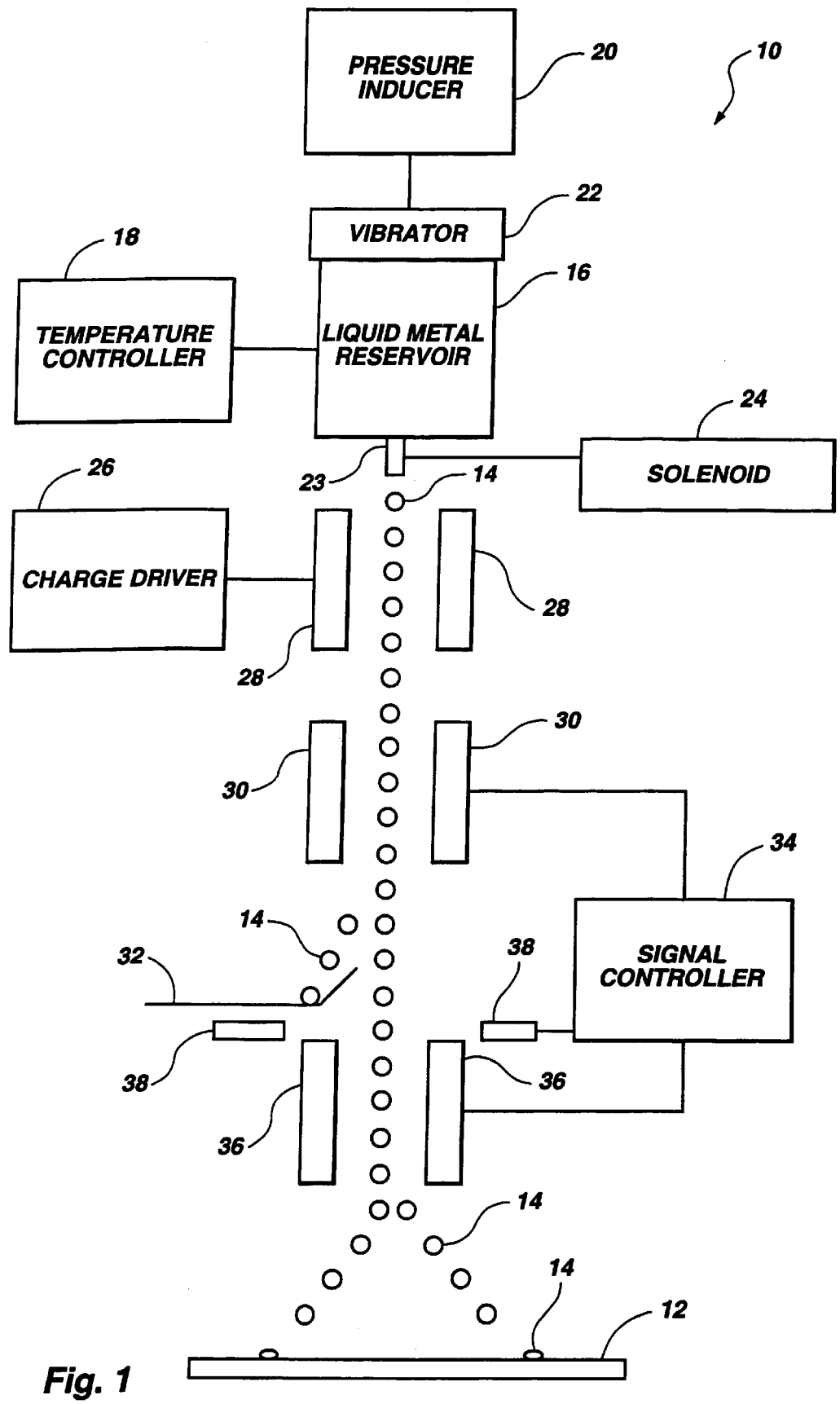
FIG. 1 is a schematic block diagram of a solder jet apparatus according to the present invention.

A solder jet apparatus 10 is depicted in the schematic block diagram of FIG. 1. Solder jet apparatus 10 deposits metal on substrate 12 in the form of solder droplets 14. The droplets 14 can be directed in an X-Y plane of deflection using a raster scan and blanking system. This allows the solder droplets to be "written" on substrate 12.

The droplets 14 are formed from melted metal held in liquid metal reservoir 16. A temperature controller 18 is connected to reservoir 16 so that the temperature of the liquid metal held in the reservoir can be kept at a desired temperature that leads to optimum droplet formation and release. For example, the solder eutectic temperature at the point of release is 190° C. and its temperature at impact is 183° C. To prevent droplets 14 from cooling too rapidly or from oxidizing, a constant surrounding temperature is provided and, if desired, the apparatus can be placed in a container that is either under vacuum or is filled with an inert gas.

The droplets 14 can be formed by the application of a driving pressure and a sufficient vibration force. The driving pressure can be provided by pressure inducer 20, which is comprised of a piezoelectric crystal that is driven by a tuning frequency sufficient enough to cause pressure to build up in reservoir 16. The mechanical vibration is generated by vibrator 22, which comprises a second piezoelectric crystal that is driven by another tuning frequency, causing reservoir 16 to vibrate. The timing of the pressure and the vibrations is established so as to produce uniform droplets of the same consistency. Once the droplets 14 are formed, the vibration releases them from reservoir 16 and the force of gravity draws them down at a predictable velocity.

Reservoir 16 further includes a solder jet nozzle 23, which is opened and closed via a solenoid 24. The aperture of nozzle 23 is selected with a size sufficient enough to generate the droplets of a desired size. The droplets 14 are formed having a diameter of micron size, ranging from 40–300. When solenoid 24 is activated, it either closes or opens nozzle 23.

Droplets 14 pass through several zones before either being deposited on substrate 12 or recycled back to reservoir 16. The first zone is a charging field driven by charge driver 26. Charge driver 26 causes charge electrodes 28 to generate an electric field therebetween. As droplets 14 pass past electrodes 28, they are imparted with an electric charge. With this charge, droplets 14 can be deflected at later stages as appropriate.

The second zone is a blanking zone that uses blanking electrodes or coil 30. The blanking electrodes are activated having sufficient electric field so as to cause droplets 14 to deflect to a catcher 32. This is the return function of the scanning function as is described below. Catcher 32 catches the liquid solder and causes the metal to be recycled to reservoir 16. This prevents droplets 14 from depositing on the surface of substrate 12. This blanking can be done in a selective manner so that droplets are deposited in some locations, but not others. Blanking electrodes or coil 30 are controlled by signal controller 34. Signal controller 34 can be a signal processor such as a computer system. The computer system allows greater control of droplets 14 by programming the electrodes or coil 30 to turn on and off in a desired sequence so as to pattern the substrate with a desired solder pattern. An alternative embodiment can include an air jet system if the electrical pulse is insufficient to remove the droplets. A photo cell can be located above the air jet system in order to insure proper timing of electrical pulses or the air pressure.

The third zone is the raster scan system and includes electrostatic deflection plates or magnetic coil 36. Plates 36 are charged by signal controller 34 so that droplets 14 are deflected in either the horizontal X-direction or the vertical Y-direction, or both. Further, the droplets 14 can be held in a steady position in the X-Y plane in order to build up the solder to a desired height. Since the droplet stream now scans in the X- and Y-directions, the substrate 12 can now stay stationary throughout the droplet application process. Signal controller 34 can be programmed to perform a variety of soldering patterns for placing droplets 14 on substrate 12. For example, a CAD/CAM system programmed with a desired output sends signals to blanking electrodes 30 and to deflection plates 36 to guide the droplet stream in the desired pattern of placing droplets in certain locations, but not in others. Additionally, when the "stream" of solder droplets 14 is returned to the beginning of the horizontal scan, blanking electrodes 30 cause the droplets 14 to deflect to catcher 32 so as not to "write" across the substrate during the return scan. The location of blanking electrodes 30 and deflection plates 36 can be switched, if desired.

An electronic light sensor 38, which connects to signal controller 34, is positioned so that the droplets 14 pass through the electronic light sensor 38. Light sensor 38 is used to count the number of droplets 14 passing by. This allows signal controller 34 to monitor the droplet output and either blank or pass droplets as needed.

Figure 2:
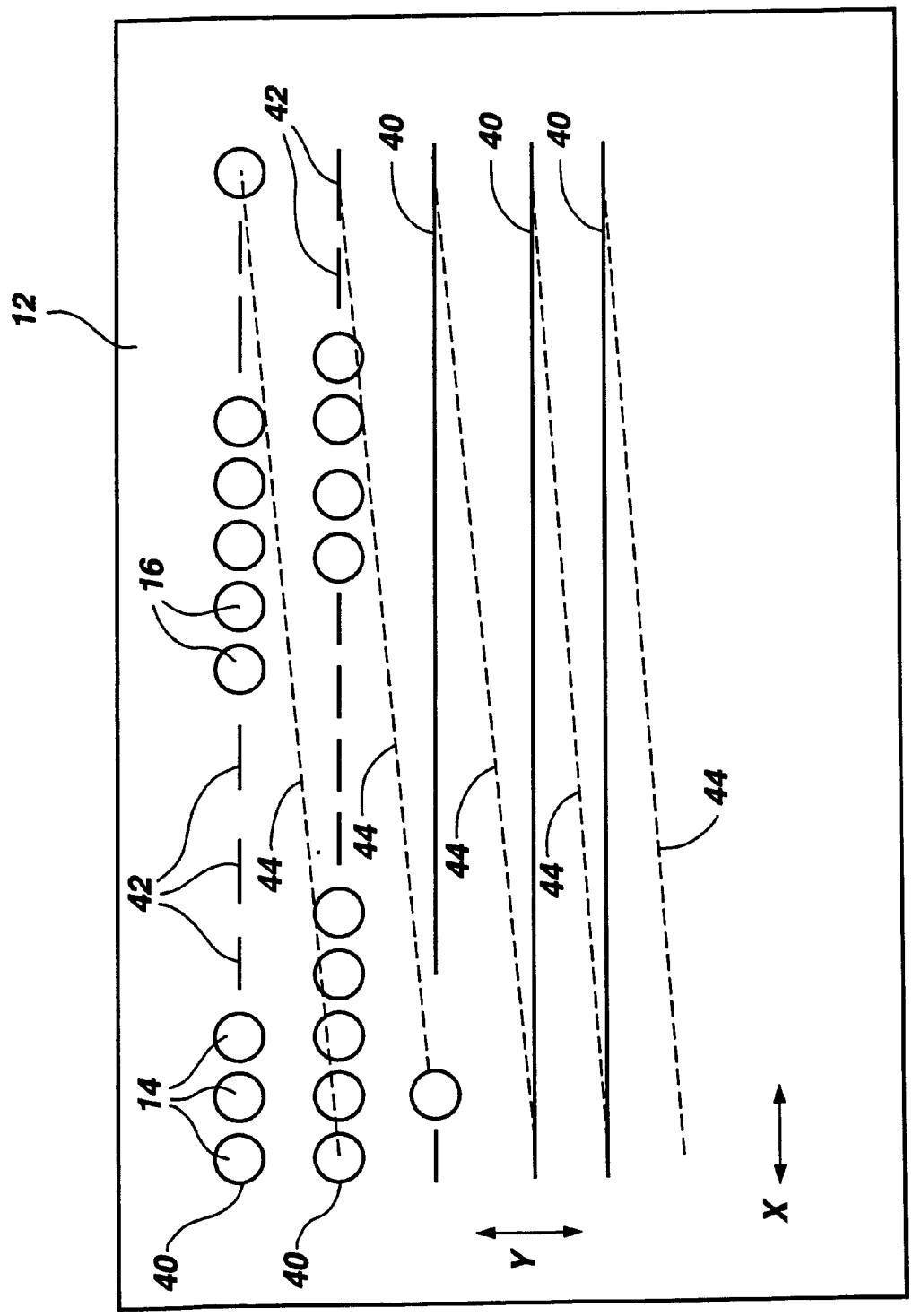
FIG. 2 is a top plan view of a substrate having solder deposited according to the solder jet apparatus of FIG. 1.

FIG. 2 is a top plan view of the surface of substrate 12 as droplets 14 are deposited. A first line 40 scans across the surface, depositing droplets 14 in selected positions and leaving blanks 42 in the remaining positions. A return scan line 44, which is ghosted, indicates when the stream of droplets is caught by catcher 32 as the stream returns to the beginning of the next line 40. This process is repeated as often as is necessary with catcher 32 collecting all the blank spots and scan returns. Alternatively, solenoid 24 can be activated to close nozzle 23 during the return scan. This also prevents unwanted droplets 14 from depositing on the surface of substrate 12.

The type of solder used with the solder apparatus 10 can include any type of metal solder such as, for example, 63/37 PbSN, 62/36/2PbSnAa, In/Sn.

The solder jet apparatus 10 can be used for many types of solder application. One type of application includes that of applying uniform solder balls, in the form of solder droplets, to the substrate 12. This provides a universal ball applicator system. Further, the system can repair particular locations where the solder ball application process has failed to insert a desired solder ball. In order to repair any and all solder ball defects, a scan of the surface of substrate 12 can be provided and then a map of the defective areas can be programmed to the signal controller 34. This allows for a rapid repair of the surface of substrate 12 where solder balls had been omitted. Another application is to pre-tin a location on substrate 12. Pre-tinning is accomplished by applying one or more droplets to the same location or to apply droplets in such a manner as to thoroughly cover the surface of substrate 12 or a grid section of substrate 12.

Similar to pre-tinning is pre-plating a board. Pre-plating a board involves applying solder droplets over the entire surface area of the board to cover it with a metal plate. An exposed portion of the board can be selected where desirable. Typically, this area is along the edge of the board either on one edge, two edges, or all four edges, or can be in the center section of the board. Prior methods of pre-plating a board resulted in a problem known as "measling." Measling is where small holes exist in the plating surface that lead to electrical defaults. The use of the solder jet apparatus 10 allows the system to eliminate the measling locations by applying solder directly to those openings. Additionally, using the pre-plating process provided by apparatus 10 eliminates measling entirely. Just as pre-plated boards may have measling problems, boards that had been stenciled with solder paste had similar problems. These problems can include openings or gaps in the stenciled design. Again, a map of the surface defects can be ascertained and then used by the signal controller 34 to make appropriate correction and repair to those particular problem points. Additionally, large areas can be printed using the X-Y motion of the table in combination with the X-Y slowing of the solder application. Also, the final ball size can be changed on demand. Further, in prior ball application systems that apply 7 balls/sec, the board needs to be moved to a new location. With this invention, no relocation time is required, thus reducing processing time.

While the present invention has been described in terms of certain preferred embodiments, it is not so limited, and those of ordinary skill in the art will readily recognize and appreciate that many additions, deletions and modifications to the embodiments described herein may be made without departing from the scope of the invention as hereinafter claimed.

What is claimed is:

1. A method for generating a continuous stream of liquid metal droplets comprising:
    producing a continuous stream of liquid metal droplets; and
    selectively directing said stream of liquid metal droplets in a first dimension and a second dimension, said selectively directing comprising:
        raster scanning said stream of liquid metal droplets; and
        blanking selectively said stream of liquid metal droplets.

2. The method according to claim 1, wherein said producing further comprises:
    heating a metal to a liquid state;
    controlling a temperature of said metal in said liquid state to maintain said metal in said liquid state.

3. The method according to claim 1, wherein said producing further comprises:
    inducing a pressure on a source of liquid metal; and
    vibrating said liquid metal to cause said liquid metal droplets to be formed as said pressure is induced on said source of liquid metal.

4. The method according to claim 3, wherein said pressure inducing is generated by a piezoelectric crystal driven by a given frequency to produce a desired pressure.

5. The method according to claim 3, wherein said vibrating is generated by a piezoelectric crystal driven by a selected frequency to produce a given vibration frequency sufficient enough to form droplets having a diameter substantially in the range of 40 microns to 300 microns.

6. The method according to claim 1, wherein said producing further comprises forming said liquid metal droplets having a substantially consistent diameter in the range of 40 microns to 300 microns.

7. The method according to claim 1, wherein said raster scanning comprises electrically charging said liquid metal droplets.

8. The method according to claim 7, wherein said raster scanning further comprises deflecting said electrically charged liquid metal droplets in said first dimension and said second dimension.

9. The method according to claim 1, wherein said blanking comprises blanking when said stream of liquid metal droplets is positioned between an endpoint of a first line and a start point of a second line.

10. The method according to claim 1, wherein said blanking further comprises:
    deflecting said stream of liquid metal droplets; and
    catching said deflected stream of liquid droplets prior to being deposited on a selected surface.

11. The method according to claim 1, wherein said selectively directing comprises programmably controlling a direction of said stream of liquid metal droplets.

* * * * *

UNITED STATES PATENT AND TRADEMARK OFFICE
CERTIFICATE OF CORRECTION

PATENT NO. : 6,350,494 B1  
DATED : February 26, 2002  
INVENTOR(S) : Warren M. Farnworth It is certified that error appears in the above-identified patent and that said Letters Patent is hereby corrected as shown below:

Title page,
Item [57], ABSTRACT,
Line 1, insert a period after "disclosed"

Column 2,
Line 46, insert a period after "disclosed"

Column 6,
Lines 14 and 17, before "range" change "the" to -- a --

Signed and Sealed this

Twenty-eighth Day of October, 2003

JAMES E. ROGAN
*Director of the United States Patent and Trademark Office*